US00PP13530P2

(12) United States Plant Patent
Zaiger et al.

(10) Patent No.: US PP13,530 P2
(45) Date of Patent: Jan. 28, 2003

(54) INTERSPECIFIC TREE NAMED: 'EARLY DAPPLE'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/045,708

(22) Filed: Jan. 15, 2002

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct interspecific tree [(Plum×Plumcot)×(Apricot×(Plum×Plumcot)]; the characteristics of the tree and its fruit are with the tree budded on 'Nemaguard' Rootstock (non-patented) and grown on Handford sandy loam soil with Storie Index rating 95, in USDA Zone 9, near Modesto, Calif., using standard commercial cultural fruit growing practices such as pruning, thinning, spraying, irrigation and fertilization. Its novelty consists of the following combination of desirable features:

1. Heavy and regular production of fruit.
2. Fruit with very good flavor and eating quality.
3. Fruit with and interesting and attractive mottled skin color.
4. Vigorous upright tree growth.
5. Fruit with high Brix (soluble solids) average 16.4°.

1 Drawing Sheet

STATEMENT REGARDING FEDERALLY SPONSORED RESEARCH AND DEVELOPMENT

Not applicable.

BACKGROUND OF THE VARIETY

Field of the Invention

In the field of plant genetics, we conduct an extensive and continuing plant-breeding program, including the organization and asexual reproduction of orchard trees, and of which almonds, apples, apricots, cherries, peaches, plums, nectarines and interspecifics are exemplary. It is against this background of our activities that the present variety of interspecific tree was originated and asexually reproduced by us in our experimental orchard located near Modesto, Stanislaus County, Calif.

PRIOR VARIETIES

Among the existing varieties of apricot, plum and interspecific trees, which are known to us and mentioned herein, 'Patterson' Apricot (U.S. Plant Pat. No. 2,877), 'Red Beaut' Plum (U.S. Plant Pat. No. 2,539) and the Interspecific tree 'Flavor Supreme' (U.S. Plant Pat. No. 6,763).

ORIGIN OF THE VARIETY

The present new variety of interspecific tree [(Plum×Plumcot)×(Apricot×(Plum×Plumcot)] was developed by us in our experimental orchard located near Modesto, Calif., as a first generation cross between proprietary lines of immediate parents, 369LD348 and 352LC74. The parentage of the maternal parent 369LD348 consists of *Prunus salicina* combined with *Prunus salicina* crossed with *Prunus armeniaca* and has in its ancestry 'Red Beaut' Plum. The pollen parent 352LC74 consists of *Prunus armeniaca* combined with *Prunus salicina* crossed with *Prunus armeniaca* and has in its ancestry 'Patterson' Apricot and Interspecific 'Flavor Supreme'. A large number of these first generation seedlings were planted and grown on their own root system, under close and careful observation, during which time one such seedling exhibited distinct and desirable fruit characteristics and was selected in 1996 for asexual propagation and commercialization.

ASEXUAL REPRODUCTION OF THE VARIETY

Asexual reproduction was performed in 1996 of the new interspecific tree by budding to 'Nemaguard' Rootstock (non-patented), as performed by us in our experimental orchard located near Modesto, Calif., and shows that all characteristics of the tree and its fruit are established and transmitted through succeeding asexual propagations.

SUMMARY OF THE VARIETY

The present new variety of interspecific tree is medium to large in size, vigorous, upright growth, and is a regular and productive bearer of large size, firm, clingstone fruit with a mild sweet flavor and very good eating quality. The fruit is further characterized by being relatively uniform throughout the tree, having firm, even ripening flesh with good storage and shipping quality. In comparison to the Interspecific tree 'Flavor Supreme' (U.S. Plant Pat. No. 6,763), the fruit is larger in size, 8 to 9 days later in maturity and more uniform in shape and size throughout the tree. In comparison to 'Red Beaut' Plum (U.S. Plant Pat. No. 2,539), the fruit of the new variety is larger in size, has heavier overall production, and is approximately 20 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old trees grown on 'Nemaguard' Rootstock (non-patented), near Modesto, Calif., with color in accordance with Munsell Book of Color.

Tree:

*Size.*—Medium to large. Usually pruned to 3 to 3.5 meters in height for economical harvesting of fruit.

*Vigor.*—Vigorous. Tree growth of 1.5 to 2 meters the first growing season. Tree pruned first dormant season and primary scaffolds are selected.

*Form.*—Upright. Usually pruned to vase shape.

*Branching habit.*—Upright. Crotch angles of approximately 30°.

*Productivity.*—Good. Thinning and spacing of fruit necessary.

*Density.*—Medium dense. Usually pruned to vase shape to provide more uniform sunlight throughout the tree for improved fruit color and healthy fruit spur growth.

*Bearer.*—Regular bearer. Adequate fruit set 3 consecutive years, no alternate bearing observed.

*Fertility.*—Self-sterile, pollenizer required.

*Hardiness.*—Hardy in all stone fruit growing areas of California. Winter chilling requirement approximately 650 hours at or below 45° F.

Trunk:

*Size.*—Medium to large. Average circumference of 32.9 cm measured 20.3 cm above ground.

*Texture.*—Medium shaggy, increases with age of tree.

*Color.*—5YR 5/2 to 5YR 4/2.

Branches:

*Size.*—Medium. Average circumference 16.5 cm measured 86.4 cm above ground. Crotch angle approximately 30°, increases with heavy crop load.

*Texture.*—New growth smooth, older growth medium rough.

*Lenticels.*—Small. Average number of 23 in 25.8 square cm surface. Average length 2.4 mm. Average width 1.05 mm. Color varies from 7.5YR 6/8 to 7.5YR 6/10.

*Color.*—New growth varies from 2.5GY 7/10 to 2.5GY 7/12. Older growth 10YR 5/8. Color darkens with age of growth.

Leaves:

*Size.*—Medium. Average length 80.2 mm. Average width 48.2 mm.

*Form.*—Oblanceolate. Slightly folded upward.

*Margin.*—Doubly serrate.

*Thickness.*—Medium.

*Surface.*—Upper surface relatively smooth, slightly indented over leaf veins, glabrous. Lower surface relatively smooth, small ridges created by midrib and pinnate veining, glabrous.

*Petiole.*—Medium. Average length 17.5 mm. Average width 1.6 mm. Color 2.5R 7/8 to 5Y 8.5/6. Varies with exposure to direct sunlight.

*Glands.*—Both reniform and globose on majority of leaves. Number varies from 2 to 4, average number 3. Size — 1.2 mm in length. Color 10R 5/4. Located on upper portion of petiole and base of leaf blade.

*Color.*—Upper surface 10Y 4/2 to 10Y 4/6. Lower surface 2.5GY 4/4 to 2.5GY 4/6.

Flower buds:

*Size.*—Medium. Average length 6.8 mm. Average diameter 4 mm.

*Form.*—Plump, free, conical, becoming elongated as bud matures.

*Hardiness.*—Hardy with respect to California winters.

*Pubescence.*—Wanting.

*Color.*—N 9/0.5.

*Pedicel.*—Medium to large. Average length 10.4 mm. Average width 0.53 mm.

*Number of buds per spur.*—Varies from 4 to 19, average 10.

Flowers:

*Size.*—Small to medium. Average height 11.9 mm. Average diameter 19.7 mm.

*Petals.*—Number 5, alternately positioned to sepals. Shape — obovate. Average length 9.4 mm. Average width 5.5 mm. Surface edges slightly cupped. Margin — entire. Color N9/.5.

*Sepals.*—Number 5, alternately arranged to petals. Shape — ovate, apex acute. Upper and lower surface glabrous. Average length 2.7 mm. Average width 2.3 mm. Color — upper surface 2.5GY 6/6, lower surface 2.5GY 6/10.

*Stamens.*—Number varies from 31 to 34, average number 32. Average filament length 5.3 mm. Filament color 10Y 9/2. Anther color 2.5Y 8.5/10.

*Aroma.*—Slight.

*Pollen.*—Present, but not strong. Self-sterile, pollenizer required. Color 2.5Y 8.5/10.

*Blooming period.*—Date of First bloom Feb. 28, 2001. Date of Petal Fall Mar. 9, 2001. Varies slightly with climatic conditions.

*Color.*—N 9/0.5.

*Pedicel.*—Thin and long. Average length 10.8 mm. Average width 0.6 mm. Color 2.5GY 6/8.

*Number of flowers per flower bud.*—Varies from 1 to 3, average 2.

Fruit:

*Maturity when described.*—Firm ripe.

*Date of first picking.*—Jun. 22, 2001.

*Date of last picking.*—Jun. 28, 2001. Varies slightly with climatic conditions.

*Size.*—Average diameter axially 65 mm. Average transversely in suture plane 66 mm. Weight 153 grams.

*Form.*—Nearly globose, slightly retuse at base.

*Suture.*—Nearly smooth, slightly flattened. Extends from base to apex.

*Ventral surface.*—Rounded.

*Apex.*—Nearly rounded. Very slight depression.

*Base.*—Retuse.

*Cavity.*—Rounded to slightly elongated in suture plane. Average depth 3.3 mm. Average breadth 9.9 mm.

Skin:

*Thickness.*—Medium. Tenacious to the flesh.

*Surface.*—Smooth.

*Bloom.*—Moderate amount.

*Color.*—Ground color varies from 10YR 7/6 to 10YR 6/8. Overspread with blotches of 7.5R 6/8 to 7.5R 5/10, leaving a random pattern of ground color highlighting the darker blotches.

Stem:

*Size.*—Average length 14.2 mm. Average width 2.1 mm, slightly enlarged at point of fruit attachment.

*Color.*—2.5GY 5/6 to 2.5GY 5/8.

Flesh:

*Ripens.*—Evenly.

*Texture.*—Meaty to slight give in flesh firmness.

*Fibers.*—Few, small, tender.

*Aroma.*—Slight.

*Amydgalin.*—Undetected.

*Eating quality.*—Very good, good balance between acid and sugar. Brix 16.4°, varies with number of fruit per tree and climatic conditions.

*Juice.*—Moderate amount, sweet, enhances flavor.

*Color.*—Varies from 5R 4/10 to 5R 6/10. Pit cavity 7.5R 3/12 to 7.5R 4/12. Color deepens with maturity.

Stone:

*Type.*—Clingstone.

*Size.*—Medium to large. Average length 26.1 mm. Average width 17 mm. Average thickness 10.2 mm.

*Form.*—Obovate.

*Base.*—Varies from straight to rounded.

*Apex.*—Acute.

*Surface.*—One long groove on each side of suture. Small, short, narrow ridges extending from base about ⅓ the distance of the stone toward apex, pitted very slightly throughout.

*Sides.*—Usually unequal, extending further from center plane on suture side.

*Ridges.*—Small, short, narrow ridges extending from base toward apex.

*Tendency to split.*—None.

*Color.*—7.5YR 8/6 when dry.

Kernal:

*Form.*—Oblong, rounded at base, acute at apex.

*Taste.*—Bitter.

*Viable.*—Yes, embryo developed.

*Size.*—Average length 15.4 mm. Average width 10.9 mm. Average breadth 5.1 mm.

*Skin color.*—5YR 6/8.

Use: Dessert. Market — local and long distance.

Keeping quality: Fair to good, held fruit for 10 days at 38° to 42° F. without shriveling, internal flesh break down, or loss of eating quality.

Shipping quality: Good, picking and packing trials of fruit gave minimal skin scarring or bruishing of fruit.

Plant disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its medium to large size, vigorous upright growth and a productive and regular bearer of large clingstone fruit with good eating quality; and in comparison to the Interspecific 'Flavor Supreme' (U.S. Plant Pat. No. 6,763), the fruit is larger, more uniform in size and 8 to 9 days later in maturity.

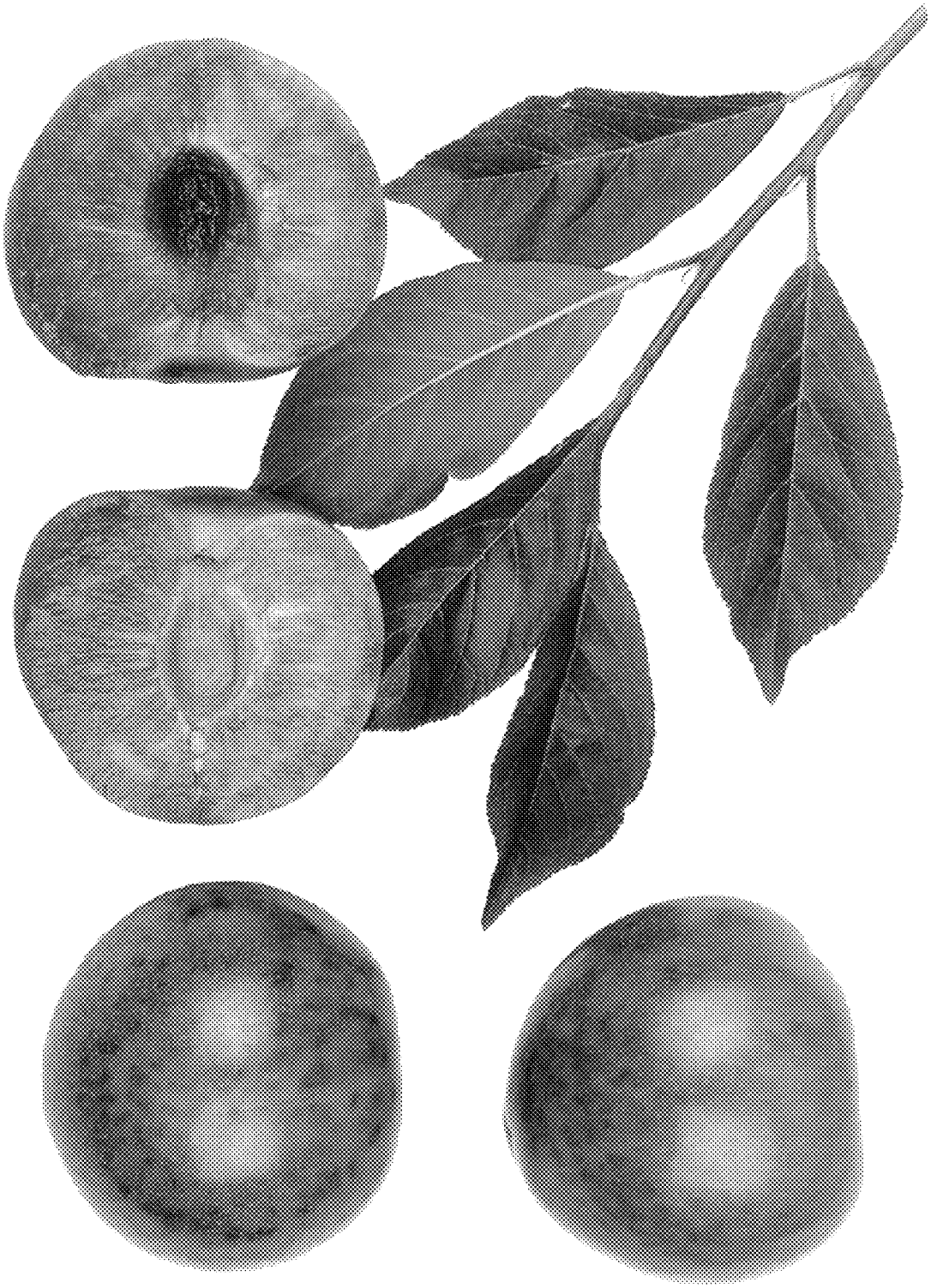

* * * * *